Oct. 15, 1974 C. G. KLEHM Plant Pat. 3,642
PEONY PLANT
Filed Oct. 26. 1973
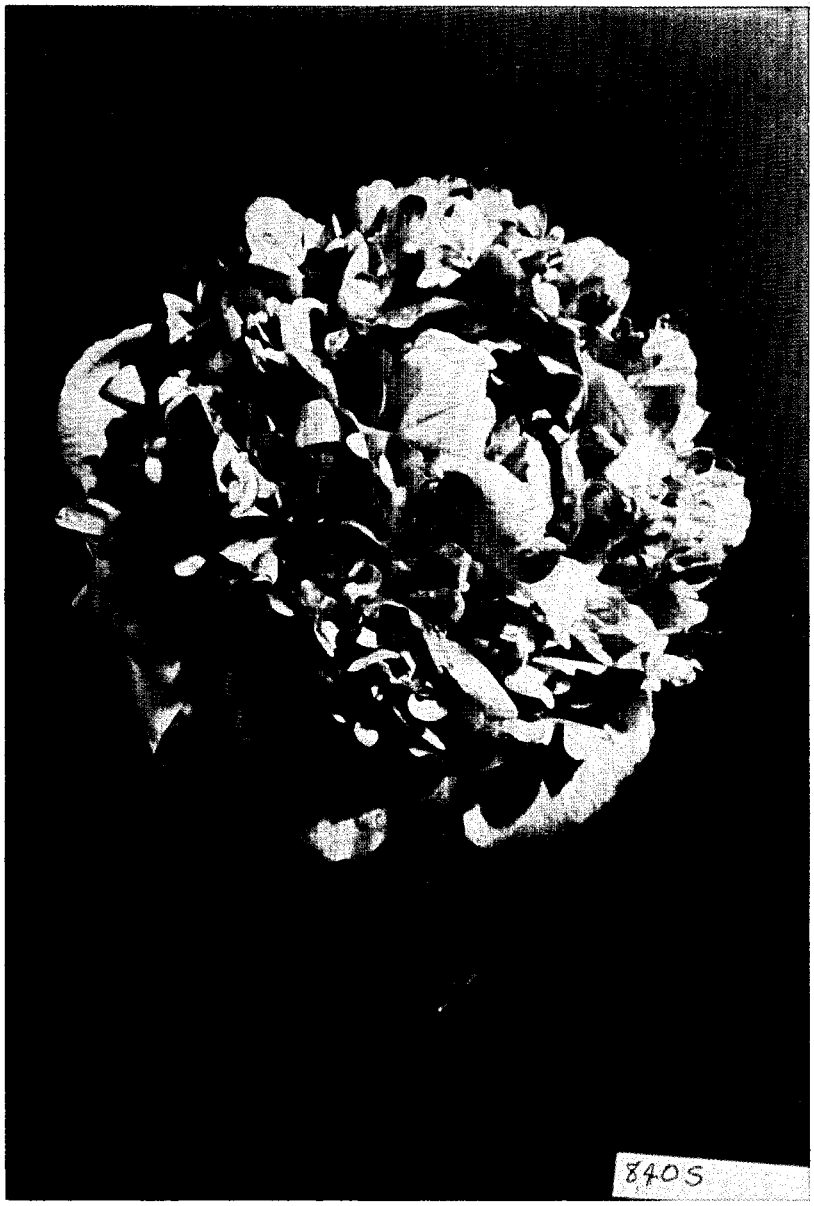

United States Patent Office

Plant Pat. 3,642
Patented Oct. 15, 1974

3,642
PEONY PLANT

Carl George Klehm, Arlington Heights, Ill., assignor to Klehm Properties, Inc., Arlington Heights, Ill.

Filed Oct. 26, 1973, Ser. No. 410,207
Int. Cl. A01h 5/00
U.S. Cl. Plt.—68 1 Claim

ABSTRACT OF THE DISCLOSURE

A new variety of *Paeonia lactiflora* having blossoms of a vibrant overall pink coloration which appear to be pervaded by an inner iridescent glow of vivid pink shades and hues, the blossom being of medium size with a pleasing bomb type of peony shape, composed of recurled and crinkled petals, carried on stiff weather and disease resistant stems of average length.

BACKGROUND OF THE NEW PLANT

This new variety of peony plant was discovered by me at my breeding grounds in Arlington Heights, Ill., and selected from among many seedlings resulting from a cross of Mons. Jules Elie (unpatented) and an unnamed and unpatented "bull" type seedling of Mons. Jules Elie maintained by me for breeding purposes and identified in my records as Seedling 71D. This plant was selected because of the very unique and vivid pink coloration of its blooms and was asexually propagated by me and under my direction, by root divisions, through many successive generations, at Arlington Heights, Illinois, to find that the unique coloring of its blooms runs true from generation to generation and appears to be firmly fixed. This plant has also been found to have inherited the exceptional strength of flowering stem and vigorous growth qualities of its seed parent Mons. Jules Elie and because it has shown a high degree of year around excellence in performance, propagation of this plant on a commercial scale, by root divisions, is now being carried on at production farms in Arlington Heights, Barrington, Champaign and Noble, Ill.

DESCRIPTION OF THE DRAWING

The new variety of peony plant herein described is illustrated by the accompanying full color photographic drawing which shows the flower in full bloom, the vivid pink color of the flower being reproduced as nearly true as it is reasonably possible to obtain by conventional professional photographic procedures.

DESCRIPTION OF THE NEW PLANT

The following is a detailed description of my new variety of peony plant with color specification according to The RHS Colour Chart published by The Royal Horticultural Society of London, England, as observed by me at Arlington Heights, Ill., during the 1973 blooming season.

THE PLANT

Origin: Seedling
Parentage:
*Seed Parent*—Mons. Jules Elie (unpatented).
*Pollen Parent*—71D, an unpatented Bull type seedling used by me exclusively for hybridization.
Classification: Botanical—*Paeonia lactiflora.*
Form: Bush, of a generally round shape.
Growth Habit: Exceptionally strong, sturdy and upright with the vigor of the seed parent.

Foliage: Normal in quantity for peony plants.
*Stems:* Stiff weather and disease resistant as observed at Arlington Heights and Barrington, Ill.
*Shape of Leaf:* Elliptically acute with smooth margins.
*Appearance:* Glossy.
*Leaflets:* Average 3 to 5 per stem.
*Ribs and Veins:* Pronounced.
*Petioles:* 2 to 4 inches in length.
*Color:* Dark Green.

THE BUD

Size: Medium—Large.
Form: Ovoid, smooth and even.
Opening Rate: Varies, depending on climatic conditions.
Color: When sepals first divide—Red-Purple Group 66C. When petals unfurl—Red-Purple Group 66C.
Sepals: Hooded over and tightly wrapped around the bud.
*Color:* Inside—Green Group 135D. Outside—Green Group 135C.

THE FLOWER

Blooming Habit: Profuse, once annually and in mid-season of peonies.
Borne: Singly with few axillary buds.
Size: Medium.
Shape: Cup-shaped with high center when bloom first opens, changing to bomb peony flower shape as blossom matures.
Petalage: Very double in number of petals.
*Arrangement:* Imbricated.
*Form:* Spatulate and curled.
*Color:* Outer petals—Red-Purple Group 66C. Inner petals—Red-Purple Group 66C. Reverse side—Red-Purple Group 66C.
*Texture:* Soft.
*Appearance:* Satiny.
*Petaloids:* None.
Fragrance: Mild peony.
Persistence: Petals drop off completely.
Discoloration After Full Bloom: None.
Lasting Quality: Above average, on plant and as a cut flower.

REPRODUCTIVE ORGANS

All reproductive organs are only rudimentary.

This new variety of peony plant is especially distinguished by the vibrant pink color of its blooms which seems to be pervaded by an iridescent inner glow of vivid pink hues and shades resulting in an unusual color that predominates all other flowers in the peony kingdom. The flower form of recurled and crinkled petals is most pleasing and the plant itself has stiff weather and disease resistant stems, clean strong foliage, and the ability to show a very high degree of year around excellence in performance.

I claim:

1. A new and distinctive variety of peony plant substantially as herein shown and described, characterized by the unique vibrant pink coloration of its blooms which have a bomb peony flower form composed of recurled and crinkled petals, by its vigorous growth habit and by its clean, strong foliage carried on stiff weather and disease resistant stems.

No references cited.

ROBERT E. BAGWILL, Primary Examiner